United States Patent
Otaka et al.

(10) Patent No.: US 10,209,055 B2
(45) Date of Patent: Feb. 19, 2019

(54) SENSOR DEVICE AND STRETCHABLE STRUCTURE

(71) Applicant: BANDO CHEMICAL INDUSTRIES, LTD., Kobe-Shi, Hyogo (JP)

(72) Inventors: Hideo Otaka, Hyogo (JP); Keizo Nonaka, Hyogo (JP); Yasuhiro Sako, Hyogo (JP); Yuki Abe, Hyogo (JP)

(73) Assignee: BANDO CHEMICAL INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 15/123,067

(22) PCT Filed: Mar. 2, 2015

(86) PCT No.: PCT/JP2015/056038
§ 371 (c)(1),
(2) Date: Sep. 1, 2016

(87) PCT Pub. No.: WO2015/133417
PCT Pub. Date: Sep. 11, 2015

(65) Prior Publication Data
US 2017/0074636 A1    Mar. 16, 2017

(30) Foreign Application Priority Data

Mar. 3, 2014  (JP) .................. 2014-040292

(51) Int. Cl.
  *G01B 7/16*  (2006.01)
  *A61B 5/11*  (2006.01)
  *G01D 5/241*  (2006.01)

(52) U.S. Cl.
  CPC .................. *G01B 7/22* (2013.01); *A61B 5/11* (2013.01); *G01D 5/2417* (2013.01); *A61B 2562/02* (2013.01)

(58) Field of Classification Search
CPC .. G01B 7/16; G01B 7/22; A61B 5/103; A61B 5/11; A61B 5/1107; G01D 5/14;
(Continued)

(56) References Cited

U.S. PATENT DOCUMENTS

| 2004/0228494 A1* | 11/2004 | Smith ............... A61B 7/04 381/67 |
| 2008/0238448 A1* | 10/2008 | Moore ............... G10H 3/10 324/686 |

(Continued)

FOREIGN PATENT DOCUMENTS

| JP | S61-73362 U | 5/1986 |
| JP | 2010-088724 A | 4/2010 |

(Continued)

OTHER PUBLICATIONS

International Search Report issued in PCT/JP2015/056038 dated Jun. 2, 2015 (1 page).

(Continued)

*Primary Examiner* — Huy Q Phan
*Assistant Examiner* — David Frederiksen
(74) *Attorney, Agent, or Firm* — Osha Liang LLP (57) ABSTRACT

A sensor device includes a sensor element, a converter, and an output unit. The sensor element includes a sheet-like dielectric layer including an elastomer composition and a top electrode layer and a bottom electrode layer each including an electroconductive composition containing carbon nanotubes. The top and the bottom electrode layers are formed on a top surface and a bottom surface of the dielectric layer, respectively, and are at least partially opposed to each other across the dielectric layer. The at least partially opposed portions of the top and the bottom electrode layers constitute a detection portion, and the dielectric layer reversibly deforms to change an area of a main surface (Continued)

of the dielectric layer. The converter electrically is connected to the sensor element and converts capacitance at the detection portion that varies in accordance with the deformation of the dielectric layer to electric characteristics.

6 Claims, 6 Drawing Sheets

(58) Field of Classification Search
CPC ........ G01D 5/24; G01D 5/2405; G01D 5/241; G01D 5/2417
See application file for complete search history.

(56) References Cited

U.S. PATENT DOCUMENTS

| | | | |
|---|---|---|---|
| 2010/0033196 A1* | 2/2010 | Hayakawa | G01B 7/22 324/686 |
| 2010/0170704 A1* | 7/2010 | Yang | H01H 13/704 174/254 |
| 2011/0006787 A1 | 1/2011 | Kadono | |
| 2011/0241704 A1* | 10/2011 | Laflamme | G01B 7/22 324/663 |
| 2013/0093437 A1* | 4/2013 | Koo | G01R 27/2605 324/660 |
| 2015/0008798 A1 | 1/2015 | Kato et al. | |
| 2016/0025669 A1* | 1/2016 | Sun | H01G 9/022 205/790.5 |
| 2016/0238368 A1* | 8/2016 | O'Brien | A61N 1/36014 |

FOREIGN PATENT DOCUMENTS

| | | | |
|---|---|---|---|
| JP | 2010088724 A | * | 4/2010 |
| JP | 2011-017626 A | | 1/2011 |
| WO | 2011/125725 A1 | | 10/2011 |
| WO | 2013/122110 A1 | | 8/2013 |

OTHER PUBLICATIONS

Written Opinion of the International Searching Authority issued in PCT/JP2015/056038 dated Jun. 2, 2015 (3 pages).

Extended European Search Report issused in corresponding European Application No. 15758016.8 dated Sep. 28, 2017 (6 pages).

* cited by examiner

SENSOR DEVICE AND STRETCHABLE STRUCTURE

TECHNICAL FIELD

The present invention relates to a sensor device, and a stretchable structure including the sensor device.

BACKGROUND ART

Recently, the number of persons with dementia has been increased year after year, and the persons with dementia are mostly elderly persons who require nursing care. Therefore, there is a strong need for an apparatus which encourages the elderly persons having a weakened muscle to actively undergo rehabilitation.

As an apparatus used for the rehabilitation, a muscle strengthening band has been proposed (for example, refer to Patent Literature 1).

The muscle strengthening band disclosed in Patent Literature 1 is used by stretching the band composed of rubber-like elastic material as main material. The muscle strengthening band has a scale or marks on its surface, so that the user can confirm a deformation amount of the band.

CITATION LIST

Patent Literature

Patent Literature 1: Japanese Utility Model Unexamined Publication No. 61-73362

SUMMARY OF INVENTION

When the muscle strengthening band (rehabilitation apparatus) disclosed in Patent Literature 1 is used by a slightly demented person and an elderly person having a bad eyesight, the scale or characters displayed on the surface of the band is hardly recognized (or cannot be recognized).

Furthermore, even when the users can recognize the deformation amount of the band at the time of use, the users are not sufficiently motivated with it to work hard for the rehabilitation and actively undergo the rehabilitation.

One or more embodiments of the present invention provide a sensor device capable of readily and surely measuring such as a deformation amount of a measuring object, and a stretchable structure including the above sensor device.

One or more embodiments of the present invention include a sensor element that includes a sheet-like dielectric layer reversely deformable in a surface direction, and electrode layers provided on both surfaces of the dielectric layer and deformable in accordance with the deformation of the dielectric layer.

A sensor device of one or more embodiments of the present invention includes a sensor element having a sheet-like dielectric layer comprising an elastomer composition, and electrode layers comprising an electroconductive composition containing carbon nanotubes and formed on a top surface and a bottom surface of the dielectric layer to be at least partially opposed to each other across the dielectric layer, in which an opposed portion of the electrode layers serves as a detection portion, and the dielectric layer is reversibly deformed to change an area of a main surface of the dielectric layer; a converter electrically connected to the sensor element and configured to convert capacitance at the detection portion varying in accordance with the deformation of the dielectric layer to electric characteristics; and an output unit configured to output information corresponding to the electric characteristics in a form recognizable by any of the five senses.

In the sensor device of one or more embodiments of the present invention, the dielectric layer is deformable to the extent that the area of the main surface is increased from a non-elongated state by 30% or more.

In the sensor device of one or more embodiments of the present invention, the information is at least one of sound information and light information.

A stretchable structure of one or more embodiments of the present invention includes a stretchable apparatus body, and the sensor device integrated with the apparatus body, wherein the sensor element stretches in response to a stretch of the apparatus body.

In the stretchable structure of one or more embodiments of the present invention, the apparatus body is an expander or a tube for rehabilitation.

According to the sensor device of one or more embodiments of the present invention, the sheet-like dielectric layer comprises an elastomer composition, and the electrode layer comprises an electroconductive composition containing carbon nanotubes in the sensor element. Therefore, the dielectric layer can be largely deformed in the surface direction, and the electrode layer can be deformed in accordance with the deformation of the dielectric layer. Therefore, according to the sensor device of one or more embodiments of the present invention, even when the measuring object is largely deformed (stretched), its deformation state can be measured.

Furthermore, according to the stretchable structure of one or more embodiments of the present invention, the sensor device is integrated with the stretchable apparatus body. Therefore, according to the stretchable structure, the deformation (stretch) state of the apparatus body can be surely recognized by the sensor device.

DESCRIPTION OF EMBODIMENTS

Hereinafter, embodiments of the present invention will be described with reference to the drawings.

A sensor device of one or more embodiments of the present invention includes a sensor element having a sheet-like dielectric layer comprising an elastomer composition, and electrode layers comprising an electroconductive composition containing carbon nanotubes and formed on a top surface and a bottom surface of the dielectric layer to be at least partially opposed to each other across the dielectric layer, in which an opposed portion of the electrode layers serves as a detection portion, and the dielectric layer is reversibly deformed to change an area of a main surface of the dielectric layer; a converter electrically connected to the sensor element and configured to convert capacitance at the detection portion varying in accordance with the deformation of the dielectric layer to electric characteristics; and an output unit configured to output information corresponding to the electric characteristics in a form recognizable by any of the five senses.

Figure 1:
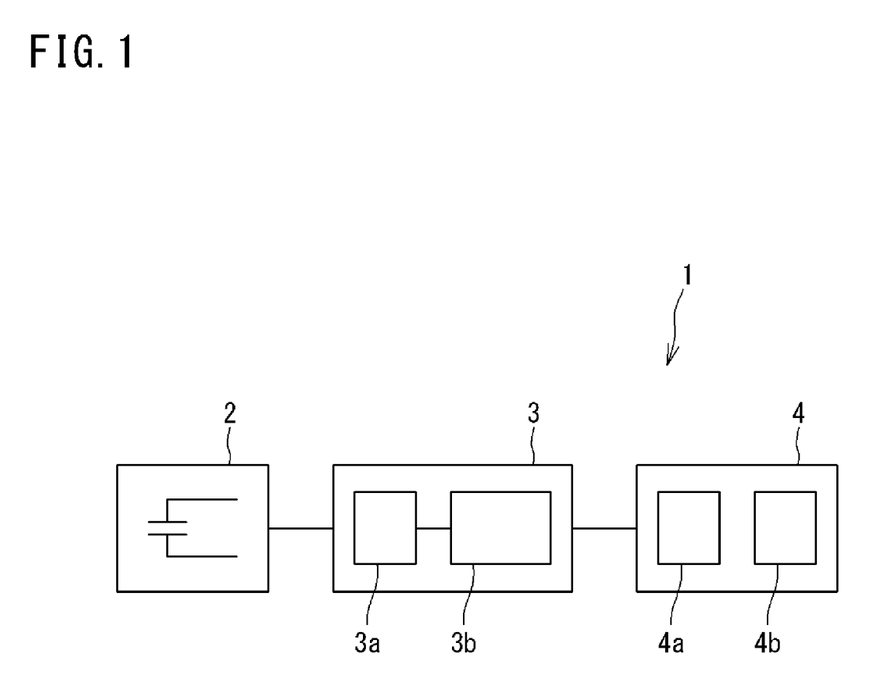
FIG. 1 is a schematic view illustrating one example of a sensor device according to one or more embodiments of the present invention.

FIG. 1 is a schematic view illustrating one example of the sensor device according to one or more embodiments of the present invention.

Figure 2A:
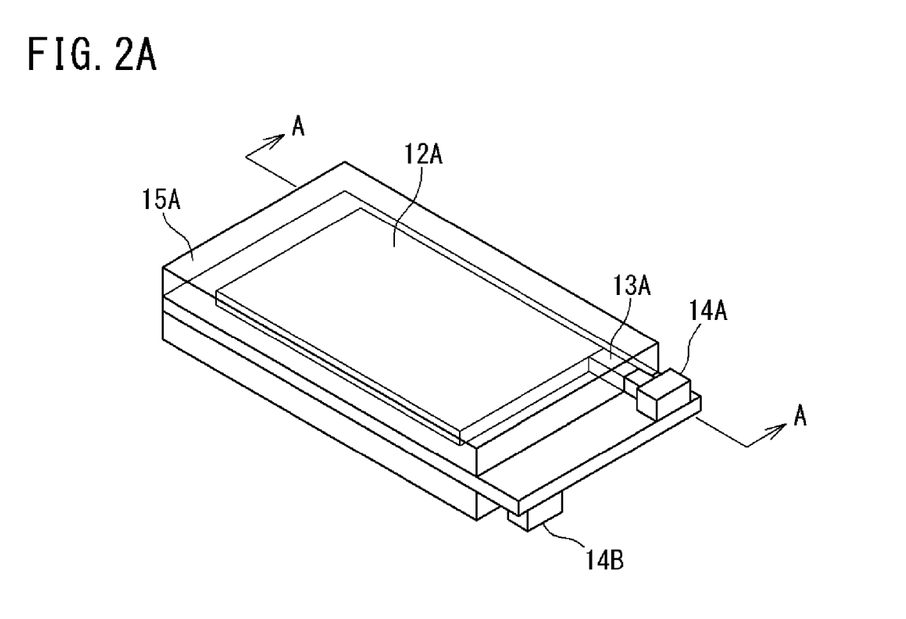
FIG. 2A is a perspective view schematically illustrating one example of a sensor element in the sensor device according to one or more embodiments of the present invention.
Figure 2B:
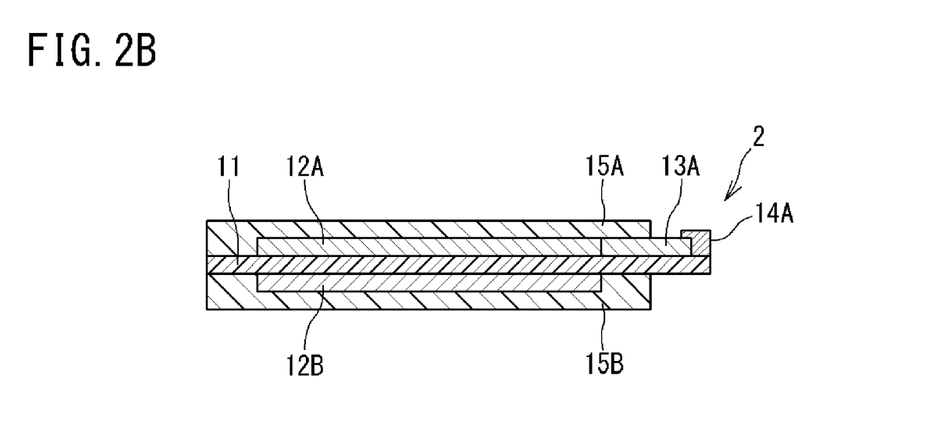
FIG. 2B is a cross-sectional view taken along a line A-A in FIG. 2A.

FIG. 2A is a perspective view schematically illustrating one example of the sensor element in the sensor device according to one or more embodiments of the present invention, and FIG. 2B is a cross-sectional view taken along a line A-A in FIG. 2A.

As illustrated in FIG. 1, a sensor device 1 of one or more embodiments of the present invention includes a sensor element 2 for detecting capacitance, a converter 3 electrically connected to the sensor element 2 and configured to convert the capacitance detected by the sensor element 2 to electric characteristics, and an output unit 4 electrically connected to the converter 3 and configured to output information corresponding to the electric characteristics in a form recognizable by the five senses, such as light emission information.

The converter 3 includes a Schmitt trigger oscillation circuit 3a for converting capacitance C to a frequency signal F, and a F/V conversion circuit 3b for converting the frequency signal F to a voltage signal V. The converter 3 converts the capacitance C detected at a detection portion of the sensor element 2 to the frequency signal F and then, further converts it to the voltage signal V, and transmits it to the output unit 4. The converter 3 may amplify the voltage signal with an amplifier (not illustrated) and then transmit it to the output unit 4.

The output unit 4 includes a PIC control circuit 4a, and an LED display 4b having a plurality of arranged LED elements having different light emission colors. The output unit 4 turns on a predetermined LED element, according to the voltage signal transmitted from the converter 3 through the PIC control circuit.

As illustrated in FIGS. 2A and 2B, the sensor element 2 includes a sheet-like dielectric layer 11 composed of the elastomer composition, a top electrode layer 12A laminated on a top surface (front surface) of the dielectric layer 11, a bottom electrode layer 12B laminated on a bottom surface of the dielectric layer 11, a top conducting wire 13A connected to the top electrode layer 12A, a bottom conducting wire 13B connected to the bottom electrode layer 12B, a top connecting portion 14A mounted on the top conducting wire 13A at an end opposite to the top electrode layer 12A, a bottom connecting portion 14B mounted on the bottom conducting wire 13B at an end opposite to the bottom electrode layer 12B, and a top protective layer 15A and a bottom protective layer 15B laminated on a top side and a bottom side of the dielectric layer 11, respectively.

The top electrode layer 12A and the bottom electrode layer 12B have the same shape in planar view, and the top electrode layer 12A and the bottom electrode layer 12B are wholly opposed to each other across the dielectric layer 11.

An opposed portion of the top electrode layer 12A and the bottom electrode layer 12B serves as the detection portion of the sensor element 2.

In addition, in one or more embodiments of the present invention, the top electrode layer and the bottom electrode layer in the sensor element are not necessarily required to be wholly opposed across the dielectric layer, and at least part of them is to be opposed.

Since the dielectric layer of the sensor element comprises the elastomer composition, it can be deformed (stretched) in a surface direction. When the dielectric layer of the sensor element is deformed in the surface direction, the top electrode layer and the bottom electrode layer (hereinafter, simply referred to as the electrode layer in a case where they are not required to be distinguished in particular), and the protective layer are also deformed in accordance with the deformation.

Thus, when the electrode layer is deformed, the capacitance of the detection portion varies in proportion to a deformation amount of the dielectric layer. Thus, when a variation in capacitance at the detection portion is detected, a deformation amount of the sensor element can be detected.

Hereinafter, each member in the sensor device of one or more embodiments of the present invention will be described in detail.

<Sensor Element>
<<Dielectric Layer>>

The dielectric layer is a sheet-like product comprising the elastomer composition. The dielectric layer is reversibly deformed such that its main surface is changed.

Examples of the elastomer composition include materials containing an elastomer, and other optional components used as required.

Examples of the elastomer include natural rubber, isoprene rubber, nitrile rubber (NBR), ethylene propylene rubber (EPDM), styrene butadiene rubber (SBR), butadiene rubber (BR), chloroprene rubber (CR), silicone rubber, fluorine rubber, acrylic rubber, hydrogen-added nitrile rubber, and urethane elastomer. They may be used alone or may be combined with one or more.

Among them, urethane elastomer and silicone rubber are used because their permanent strain (or permanent elongation) is low. Furthermore, compared with the silicone rubber, the urethane elastomer may also be used because it is excellent in adhesion with carbon nanotubes.

The urethane elastomer is produced through a reaction between a polyol component and an isocyanate component. Specific examples thereof include an olefin-based urethane elastomer containing olefin-based polyol as the polyol component, an ester-based urethane elastomer containing ester-based polyol as the polyol component, an ether-based urethane elastomer containing ether-based polyol as the polyol component, a carbonate-based urethane elastomer containing carbonate-based polyol as the polyol component, and a castor oil-based urethane elastomer containing castor oil-based polyol as the polyol component. They may be used singly, or may be used in combination of two or more. Furthermore, the urethane elastomer may be composed of the above two or more polyol components.

Examples of the olefin-based polyol include EPOL (produced by Idemitsu Kosan Co., Ltd.).

In addition, examples of the ester-based polyol include POLYLITE 8651 (produced by DIC Corporation).

Furthermore, examples of the ether-based polyol include poly oxytetramethylene glycol, PTG-2000SN (produced by Hodogaya Chemical Co., Ltd.), polypropylene glycol, PREMINOL S3003 (produced by Asahi Glass Co., Ltd.), or PANDEX GCB-41 (produced by DIC Corporation).

In addition, in synthesizing the urethane elastomer, agents such as a chain extender, a cross-linker, a catalyzer, and a vulcanization accelerator may be added during its reaction as required.

Furthermore, the elastomer composition may contain additive agents such as a plasticizer, an antioxidant, an age resistor, and a colorant, other than elastomer.

Furthermore, the elastomer composition may contain such as barium titanate as a dielectric filler. Thus, the capacitance C of the dielectric layer can be increased, and as a result, the sensor element can be high in detection sensitivity.

In the case where the dielectric filler is contained, its amount contained in the elastomer composition is normally about more than 0% by volume and equal to or less than 25% by volume. When the content of the dielectric filler exceeds 25% by volume, the dielectric layer is increased in hardness, and the permanent strain is increased in some cases. In addition, when the dielectric layer is formed of urethane elastomer, it is difficult to make the dielectric layer have a uniform thickness in some cases because liquid viscosity before curing is high.

An average thickness of the dielectric layer is 10 µm to 1000 µm, or 30 µm to 200 µm in view of increasing the capacitance C to improve the detection sensitivity, and in view of improving followability with respect to a measuring object.

The dielectric layer can be deformed such that its main surface area is increased from a non-elongation state by 30% or more. When the dielectric layer having those characteristics is attached to the measuring object and used, it is favorably deformed in accordance with the deformation of the measuring object.

Here, being able to be deformed such that the area is increased by 30% or more means that even when a load is applied and the area is increased by 30%, the dielectric layer is not broken, and when the load is released, it is restored to its original state (that is, elastic deformation is provided).

A deformable range of the dielectric layer with an increase of the area of the main surface is 50% or more, 100% or more, or 200% or more.

The deformable range of the dielectric layer in the surface direction can be controlled by a design (such as material or shape) of the dielectric layer.

Relative permittivity of the dielectric layer at room temperature is 2 or more, or 5 or more. When the relative permittivity of the dielectric layer is less than 2, the capacitance C is low, and sufficient sensitivity as the sensor element may not be obtained.

Furthermore, Young's modulus of the dielectric layer is 0.1 MPa to 10 MPa. When the Young's modulus is less than 0.1 MPa, the dielectric layer is too soft, and a high-quality process is difficult to perform, so that measurement accuracy may not be sufficiently high. Meanwhile, when the Young's modulus exceeds 10 MPa, the dielectric layer is too hard, so that when it is mounted on a stretchable apparatus body, the apparatus body could be hardly deformed.

The hardness of the dielectric layer is 0° to 30° when measured by type A durometer (JIS A hardness) based on JIS K 6253, or 10° to 55° when measured by type C durometer (JIS C hardness) based on JIS K 7321.

When the dielectric layer is too soft, the high-quality process is hard to perform, so that measurement accuracy may not be sufficiently high. However, in the case where the dielectric layer is too hard, when it is mounted on the stretchable apparatus body, the apparatus body could be hardly deformed.

<<Electrode Layer>>

The electrode layer (including the top electrode layer and the bottom electrode layer) comprises an electroconductive composition containing carbon nanotubes.

As the carbon nanotube, publicly known carbon nanotubes can be used. That is, the carbon nanotube may be a single-walled carbon nanotube (SWNT), a double-walled carbon nanotube (DWNT), or a multi-walled carbon nanotube (MWNT) (these are simply referred to as the multi-walled carbon nanotube in this specification). Furthermore, two or more kinds of carbon nanotubes having the different number of walls may be combined.

Furthermore, a shape (average length, fiber diameter, or aspect ratio) of each carbon nanotube is not limited in particular, and it may be appropriately selected in view of various factors such as intended use of the sensor device, electric conductivity and durability required for the sensor element, and processes and costs to form the electrode layer.

An average length of the carbon nanotubes is 50 µm or more.

Thus, when the electrode layer is formed of the carbon nanotubes having the large fiber length, excellent characteristics are provided, that is, the electric conductivity is high, and even when it is deformed (especially elongated) in accordance with the deformation of the dielectric layer, its electric resistance is hardly increased, and even when it is repeatedly stretched, its variation in electric resistance is small.

Meanwhile, when the average length of the carbon nanotubes is less than 50 µm, the electric resistance could be increased with the deformation of the electrode layer, and the electric resistance could largely vary after the electrode layer has been repeatedly stretched. Especially, when the deformation amount of the sensor element (dielectric layer) is increased, such defect is likely to be generated.

An upper limit of the average length of the carbon nanotubes is 1000 µm. The carbon nanotubes having the average length exceeding 1000 µm are hard to manufacture and obtain at the moment. In addition, as will be described below, when a dispersion liquid of the carbon nanotube having the average length exceeding 1000 µm are applied to form the electrode layer, a conducting path is not likely to be formed because the carbon nanotubes may not be sufficiently dispersed, so that the electric conductivity of the electrode layer may not be sufficiently high.

A lower limit of the average length of the carbon nanotubes is 100 µm, and an upper limit thereof is 600 µm. When the average length of the carbon nanotubes falls within the above range, the excellent characteristics can be more surely ensured at high level, that is, the electric conductivity is high, the electric resistance is hardly increased at the time of stretching, and the variation in electric resistance is small even after the repeated stretching.

A fiber length of the carbon nanotube may be measured from an image obtained by observing the carbon nanotubes with an electron microscope.

In addition, the average length of the carbon nanotubes may be obtained by calculating an average value based on ten carbon nanotube fiber lengths randomly chosen from the observed image of the carbon nanotubes.

An average fiber diameter of the carbon nanotubes is not limited in particular, and it is 0.5 nm to 30 nm.

When the fiber diameter is less than 0.5 nm, the carbon nanotubes are not well dispersed, and as a result, the conducting path may not expand and the electric conductivity of the electrode layer may not be sufficiently high. Meanwhile, when it exceeds 30 nm, the number of the carbon nanotubes is reduced while a weight is the same, so that the electric conductivity may not be sufficiently high. The average fiber diameter of the carbon nanotubes is 5 nm to 20 nm.

As for the carbon nanotube, the multi-walled carbon nanotube is used more than the single-walled carbon nanotube.

In the case of using the single-walled carbon nanotube, even when the carbon nanotube to be used has the average length falling within the above-described range, the electric resistance could become high, the electric resistance could be largely increased at the time of stretching, or the electric resistance could largely vary after the repeated stretching.

The reason for this is considered as follows. That is, the single-walled carbon nanotubes are commonly synthesized as a mixture of a metallic carbon nanotubes and a semiconductive carbon nanotubes, so that the semiconductive carbon nanotubes assumedly causes the electric resistance to become high, the electric resistance to largely increase at the time of stretching, or the electric resistance to largely vary after the repeated stretching.

Here, by separating the metallic carbon nanotubes and the semiconductive carbon nanotubes and only using the metallic single-walled carbon nanotubes having the large average length, it is considered possible to form an electrode layer having the same electric characteristics as those obtained by using the multi-walled carbon nanotubes having the large average length. However, it is very difficult to separate the metallic carbon nanotubes and the semiconductive carbon nanotubes (especially in the case where the carbon nanotubes have the large fiber length), so that a complicated process is required to separate them. Therefore, as described above, the multi-walled carbon nanotubes are used as the carbon nanotubes in view of processability to form the electrode layer and costs.

The carbon nanotubes have carbon purity of 99% by weight or more. The carbon nanotubes may include a catalyst metal, a dispersant or the like in the production process of the carbon nanotubes, and when the carbon nanotubes containing a large amount of such components other than the carbon nanotube (impurities) are used, the electric conductivity could be lowered, and the electric resistance could vary.

The carbon nanotubes may be manufactured by a conventionally known method, and it is manufactured by a substrate growth method.

The substrate growth method is one of CVD methods, in which the carbon nanotube is grown and manufactured by supplying a carbon source to a metal catalyst applied on a substrate. The substrate growth method is a suitable method for manufacturing the carbon nanotubes having a relatively long and uniform fiber length. Therefore, this method is suitable for manufacturing the carbon nanotube used in one or more embodiments of the present invention.

In the case where the carbon nanotubes are manufactured by the substrate growth method, the fiber length of the carbon nanotube is substantially equal to a length of growth of a CNT forest. Therefore, when the fiber length of the carbon nanotube is measured with the electron microscope, the length of growth of the CNT forest is to be measured.

The electroconductive composition may contain a binder component other than the carbon nanotubes.

The binder component functions as a binding material, and when the binder component is contained, adhesion between the electrode layer and the dielectric layer, and the strength of the electrode layer itself can be improved. Furthermore, when the binder component is contained, the carbon nanotubes are prevented from being scattered when the electrode layer is formed by a method which will be described below, so that safety can be enhanced at the time of forming the electrode layer.

Examples of the binder component include butyl rubber, ethylene propylene rubber, polyethylene, chlorosulfonated polyethylene, natural rubber, isoprene rubber, butadiene rubber, styrene butadiene rubber, polystyrene, chloroprene rubber, nitrile rubber, polymethylmethacrylate, polyvinyl acetate, polyvinyl chloride, acrylic rubber, and styrene-ethylene-butylene-styrene block copolymer (SEBS).

Furthermore, the binding component may be a raw rubber (an unvulcanized natural rubber and an unvulcanized synthetic rubber). When the raw rubber having relatively low elasticity is used, the followability of the electrode layer with respect to the deformation of the dielectric layer can be enhanced.

The binding component has a solubility parameter (SP value $[cal/cm^3)^{1/2}]$) which is close to that of the elastomer in the dielectric layer, and an absolute value of a difference between their soluble parameters (SP values) is 1 or less. This is because as the solubility parameters come closer, the adhesion between the dielectric layer and the electrode layer is improved. The SP value in one or more embodiments of the present invention is calculated by Fedors's prediction method.

The binder component is the same kind as the elastomer in the dielectric layer because the adhesion between the dielectric layer and the electrode layer can be remarkably improved.

The electroconductive composition may further contain various additive agents other than the carbon nanotube and the binder component. Examples of the additive agents include a dispersion agent to improve dispersibility of the carbon nanotube, a cross-linker for the binder component, a vulcanization accelerator, a vulcanization aid, an age resistor, a plasticizer, a softener, and a colorant.

Here, in a case where the electroconductive composition contains the plasticizer, and the elastomer composition in the dielectric layer also contains the plasticizer, a concentration of the plasticizer is equal in both compositions. The reason for this is that a transition of the plasticizer between the dielectric layer and the electrode layer can be prevented, and the occurrence of warpage and wrinkle in the sensor element can be suppressed.

The electrode layer in the sensor element may be made of substantially carbon nanotubes alone. In this case also, sufficient adhesion with the dielectric layer can be provided. In this case, the carbon nanotube and the dielectric layer are strongly adhered by van der Waals force.

An amount of the carbon nanotubes contained in the electrode layer is not limited in particular as long as the electric conductivity can be provided. While the amount of the carbon nanotubes depends on the kind of the binder component when the binder component is contained, it is 0.1% by weight to 100% by weight with respect to a total amount of the solid components in the electrode layer.

Furthermore, as the amount of the carbon nanotubes is increased, the electric conductivity of the electrode layer can be improved. Therefore, even when the electrode layer is thinned, the required electric conductivity can be ensured. As a result, it becomes easier to thin the electrode layer and ensure flexibility of the electrode layer.

An average thickness of the electrode layer is 0.1 µm to 10 µm. When the average thickness of the electrode layer falls within the above range, the electrode layer can attain the more excellent followability with respect to the deformation of the dielectric layer.

Meanwhile, when the average thickness is less than 0.1 µm, the electric conductivity is not sufficiently high, and measurement accuracy of the sensor element could be lowered. Meanwhile, when the average thickness exceeds 10 µm, the sensor element becomes hard due to stiffening effect of the carbon nanotube, so that stretchability of the sensor element is lowered. As a result, when the sensor element is attached to the stretchable apparatus body, the followability with respect to the apparatus body could be lowered, or the deformation of the apparatus body could be prevented.

In one or more embodiments of the present invention, "the average thickness of the electrode layer" can be measured with a laser microscope (such as VK-9510 manufactured by KEYENCE CORPORATION). More specifically, the electrode layer formed on the surface of the dielectric layer is scanned in a thickness direction at intervals of 0.01 µm, and its 3-dimensional shape is measured. Then, in the region having the electrode layer on the dielectric layer and the region not having the electrode layer on the dielectric layer, respective average heights are measured in rectangular regions of 200 µm×200 µm and a difference between the average heights is regarded as the average thickness of the electrode layer.

Transparency of the electrode layer is not limited in particular, and it may be transparent (transmittance of visible light (550 nm) is 85% or more, for example) or it may be opaque. Furthermore, in the case where the electrode layer is to be transparent, the carbon nanotubes are required to be subjected to a pretreatment such as high-level dispersion process and purification process, which complicates the process for forming the electrode layer, and causes an economic disadvantage. Meanwhile, the transparency of the electrode layer does not affect the performance of the electrode layer as a capacitive sensor sheet. Therefore, when the transparency is required in the capacitive sensor sheet, the transparent electrode layer is to be formed, and when it is not required, the opaque electrode layer is to be formed.

<<Others>>

The sensor element may include the top conducting wire and the bottom conducting wire connected to the electrode layers as required, as illustrated in the example in FIG. 2.

The conducting wires (the top conducting wire and the bottom conducting wire) may be made of any material as long as the deformation of the dielectric layer is not hindered, and its electric conductivity is maintained even when the dielectric layer is deformed. As a specific example, the conducting wire may be made of the same material as the electrode layer.

Furthermore, as illustrated in the example in FIG. 2, the top connecting portion and the bottom connecting portion to be connected to external wires may be formed on the top conducting wire and the bottom conducting wire at the ends opposite to the electrode layers, respectively as required. The bottom connecting portion may be formed of copper foil, for example.

As illustrated in the example in FIG. 2, the sensor element may has the protective layer (the top protective layer and/or bottom protective layer) laminated on the top outermost layer and/or the bottom outermost layer, as required.

When the protective layer is provided, the strength and durability can be enhanced in the sensor element, and the surface of the sensor element can be a non-adhesive surface.

Material of the protective layer is not limited in particular, and it may be selected according to its required characteristics. As a specific example, it includes the same material as that of the dielectric layer.

In a case where stretching is repeated 1000 cycles in which one cycle means that the sensor element is stretched in one axial direction by 100% from a non-elongation state and returned to the non-elongation state, the sensor element has a small change rate between the electric resistance when the electrode layer is stretched by 100% in the second cycle, and the electric resistance when the electrode layer is stretched by 100% in the 1000th cycle (an absolute value of [electric resistance value when stretched by 100% in the 1000th cycle—electric resistance value when stretched by 100% in the second cycle]/[electric resistance value when stretched by 100% in the second cycle]×100). More specifically, it is 10% or less, or 5% or less.

Here, the reason why the electric resistance value of the electrode layer in the second cycle instead of the first cycle is used is that a behavior of the electrode layer (fluctuation of the electric resistance) when the electrode layer is stretched from the non-elongation state for the first time (in the first cycle) considerably differs from those after the second time (second cycle). This is considered due to the fact that the state of the carbon nanotubes in the electrode layer is not stabilized until the sensor element is once stretched after it has been manufactured.

The sensor element is manufactured through the following steps. That is, the sensor element is manufactured through (1) a step of forming the dielectric layer with the elastomer composition (step (1)), and (2) a step of forming the electrode layers (the top electrode layer and the bottom electrode layer) by applying the composition containing the carbon nanotubes and a dispersion medium, on the dielectric layer.

[Step (1)]

In this step, the dielectric layer is formed of the elastomer composition.

First, a raw material composition is prepared such that an elastomer (or its raw material) is mixed with additive agents such as a chain extender, a cross-linker, a vulcanization accelerator, a catalyzer, a dielectric filler, a plasticizer, an antioxidant, an age resistor, and a colorant as required. After that, the raw material composition is formed into the dielectric layer. Furthermore, its forming method may be a conventionally known method.

More specifically, when the dielectric layer containing urethane elastomer is formed, the following method may be used.

First, a mixture is prepared by measuring the polyol component, the plasticizer, and the antioxidant, and mixing and stirring them with heat for a predetermined time under reduced pressure. Then, the mixture is measured and its temperature is adjusted, and the catalyzer is added and stirred with such as an agitator. After that, a predetermined amount of the isocyanate component is added and stirred with such as the agitator, and the mixture is immediately poured in a forming apparatus illustrated in FIG. 3, and cross-linked and cured while it is sandwiched by protective films and transferred, whereby a rolled sheet with the protective films having a predetermined thickness is obtained. After that, it is cross-linked in a furnace for a predetermined time, whereby the dielectric layer is manufactured.

Figure 3:
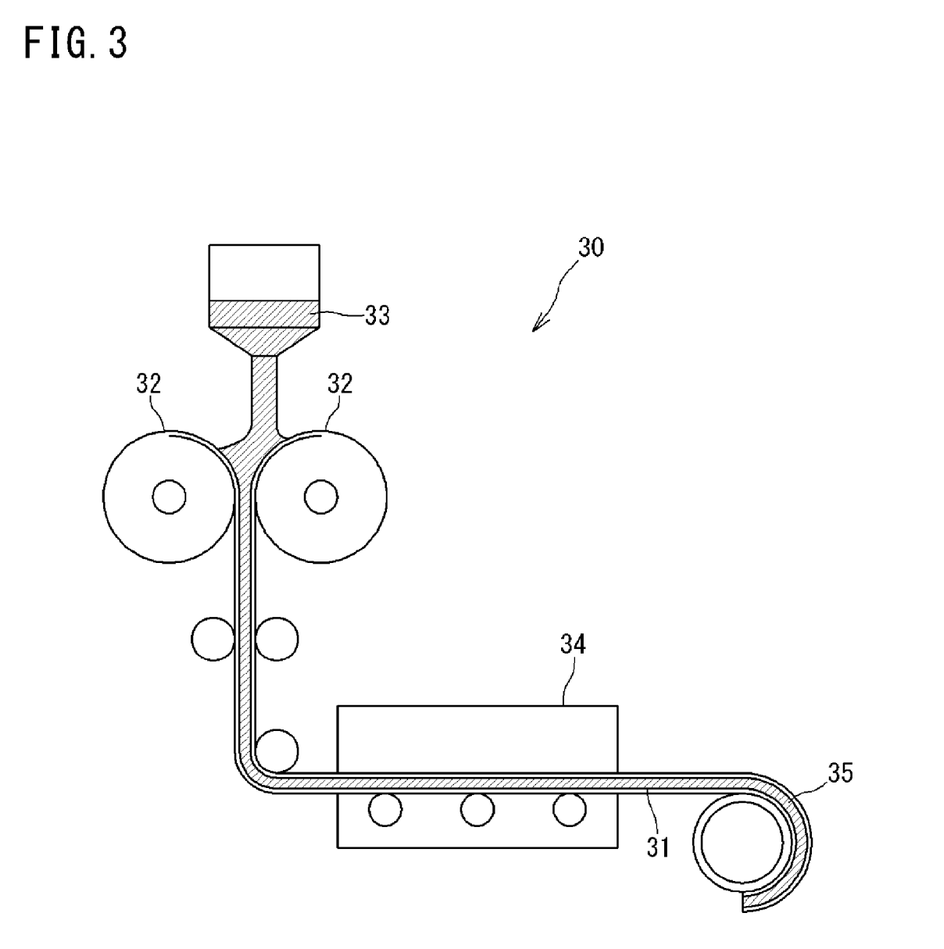
FIG. 3 is a schematic view to describe one example of a forming apparatus to be used to manufacture a dielectric layer in the sensor device according to one or more embodiments of the present invention.

FIG. 3 is a schematic view to describe one example of the forming apparatus used to manufacture the dielectric layer.

A forming apparatus 30 illustrated in FIG. 3 forms a sheet-like dielectric layer 35 in such a manner that a raw material composition 33 is poured between protective films 31 made of polyethylene terephthalate (PET) and sequentially rolled out from a pair of separately disposed rolls 32 and 32, and while the raw material composition 33 is cured (cross-linked) in a sandwiched state, the raw material composition 33 is introduced into a heating apparatus 34 to be thermally cured between the pair of protective films 31.

The dielectric layer may be manufactured with various coating apparatuses, a general-purpose film-forming apparatus such as bar coater or doctor blade by a general film-forming method after the raw material composition has been prepared.

[Step (2)]

In this step, the composition containing the carbon nanotubes and the dispersion medium (carbon nanotube dispersion liquid) is applied, and then the dispersion medium is removed in a drying process, whereby the electrode layer is formed to be integrated with the dielectric layer.

More specifically, the carbon nanotubes are added to the dispersion medium. At this time, the above-described other component such as binder component (or a raw material of the binder component) and a further dispersion agent may be added as required.

Subsequently, the components including the carbon nanotubes are dispersed (or dissolved) in the dispersion medium with a wet dispersion machine, whereby an application liquid (carbon nanotube dispersion liquid) is prepared. More specifically, the components containing the carbon nanotubes may be dispersed with an existing dispersion machine such as ultrasonic dispersion machine, jet mill, or bead mill.

Examples of the dispersion medium include toluene, methyl isobutyl ketone (MIBK), alcohol, and water. These dispersion media may be used singly, or may be used in combination of two or more thereof.

In the application liquid, a concentration of the carbon nanotubes is 0.01% by weight to 10% by weight. When the concentration is less than 0.01% by weight, the concentration of the carbon nanotubes is too low, and the liquid needs to be applied several times in some cases. Meanwhile, when it exceeds 10% by weight, viscosity of the application liquid becomes too high, and the carbon nanotubes are not likely to be dispersed due to re-aggregation, so that the uniform electrode layer is difficult to form in some cases.

Subsequently, the application liquid is applied to a predetermined position on the surface of the dielectric layer by a method such as spray coating, and then dried. At this time, the application liquid may be applied after masking material has been applied to a position other than the position of the electrode layer on the dielectric layer as required.

A drying condition of the application liquid is not limited in particular, and it may be appropriately selected according to the kind of the dispersion medium and a condition of the elastomer composition.

Furthermore, the method for applying the application liquid is not limited to the spray coating. It includes such as screen printing and ink jet printing as other application methods.

Furthermore, depending on the situation, before the electrode layer is formed, a pretreatment may be performed on the surface of the dielectric layer in order to enhance the adhesion between the dielectric layer and the electrode layer. However, the electrode layer made of the carbon nanotube, and the dielectric layer are connected with extremely high adhesion. Therefore, even when the pretreatment is not performed, sufficient adhesion can be ensured between the dielectric layer and the electrode layer.

After the dielectric layer and the electrode layer have been formed through the above steps (1) and (2), the conducting wires (the top conducting wire and the bottom conducting wire) are formed to be connected to the electrode layers, and the connecting portions (the top connecting portion and the bottom connecting portion) are formed as required.

The conducting wire to be connected to the electrode layer is formed by the same method as used to form the electrode layer such that the carbon nanotube dispersion liquid (application liquid) is applied to a predetermined position and dried. Furthermore, the conducting wire may be simultaneously formed with the electrode layer.

The connecting portion may be formed by attaching copper foil at the predetermined end of the conducting wire, for example.

Furthermore, after the electrode layer has been formed, and the conducting wire and the connecting portion have been formed as required, the protective layer may be formed on the outermost layer on the top side and/or bottom side.

The protective layer may be formed such that a sheet-like elastomer composition is formed by the same method as described in the step (1), cut into a predetermined size, and laminated.

Furthermore, in the case where the sensor element includes the protective layer, the sensor element may be manufactured such that the bottom protective layer is formed first, and then the component members (the bottom electrode layer, the dielectric layer, the top electrode layer, and the top protective layer) are sequentially laminated thereon.

Through the above steps, the sensor element is manufactured.

The sensor element illustrated in FIGS. 2A and 2B has the one detection portion, but the number of the detection portion is not limited to one in the sensor element of the sensor device of one or more embodiments of the present invention, and the plurality of detection portions may be provided.

In a specific example of the sensor element having the plurality of detection portions, the sensor element may be provided such that a plurality of rectangular electrode layers are formed and arranged in rows on the top surface and the bottom surface of the dielectric layer as the top electrode layers and the bottom electrode layers, and the row of the top electrode layer is perpendicular to the row of the bottom electrode layer in planar view. In this sensor element, each portion in which the top electrode layer and the bottom electrode layer are opposed across the dielectric layer serves as the detection portion, and the detection portions are arranged in a lattice shape.

<Converter>

The converter is electrically connected to the sensor element. The converter has the function of measuring the capacitance at the detection portion which varies in accordance with the deformation of the dielectric layer, and converting the capacitance to other electric characteristics.

A method for converting the capacitance to other electric characteristics is not limited in particular, and a conventionally known method may be used. The other electric characteristics include such as a frequency signal and a voltage signal.

A method for converting the capacitance to the frequency signal is not limited in particular, and a conventionally known method may be used. For example, the method may use the above-described Schmitt trigger oscillation circuit.

The method using the Schmitt trigger oscillation circuit is suitable to reduce the sensor device in size, and an oscillator (sensor device) can be provided at low costs.

The above converter may further convert the frequency signal to the voltage signal. This conversion is performed with a known F/V conversion circuit. Here, the capacitance may be directly converted to the voltage signal with a publicly known method as a matter of course.

The converter converts the capacitance to the other electric characteristics and then transmits such as the frequency signal or the voltage signal to the output unit.

In addition, the converter may divide the frequency signal to two signals after it has converted the capacitance to the frequency signal with such as the Schmitt trigger oscillation circuit, and then convert one signal to another signal such as the voltage signal as described above while the other signal is sent as it is to the output unit as the frequency signal. As a matter of course, the signal may be divided into three or more signals.

The converter may include an amplifier for amplifying such as the frequency signal and the voltage signal, and a frequency divider for converting a frequency of the frequency signal and the like.

The electric characteristics (electric signals) to which the capacitance is converted by the converter in the sensor element are to be determined based on the kind of the information given from the output unit.

<Output Unit>

The output unit has the function of outputting the information which corresponds to the electric characteristics (electric signals) from the converter and is recognizable by any of the five senses.

The information recognizable by any of the five senses is information visually or aurally recognized. Especially, it is light emission information (light information) using such as the LED elements as described above, or sound information. This is because the user can easily and surely recognize such information, and also get the information in the course of using the sensor device (while the sensor device is used).

In addition, the kind of the information to be given can be selected based on the condition of the user (for example who may have bad eyes but have normal ears, or the other way around).

Like the example illustrated in FIG. 1, in the case where the output unit is composed of the PIC control circuit and the LED display having the plurality of arranged LED elements, the LED display, for example, may have a configuration in which all the LED elements are off when the sensor element is not deformed yet, and as a deformation amount of the sensor element is increased, the number of the LED elements to be turned on is gradually increased. In addition, in the LED display, each LED element may emit a different color or emit the same color. Furthermore, the LED element in the LED display may be changed in light emission intensity. Still furthermore, the LED display may have the one LED element.

Furthermore, in the case where the sensor device of one or more embodiments of the present invention includes the PIC control circuit as illustrated in FIG. 1, the function of the converter may be combined in the PIC control circuit.

In the case where the output unit outputs the sound information, the output unit includes an audio amplifier and a speaker, and it is configured such that a sound pitch is changed (for example, high pitch sound is generated when the deformation amount is small, while low pitch sound is generated when the deformation amount is large), or a sound volume is changed in accordance with the magnitude of the deformation amount of the sensor element.

In addition, when the output unit gives the sound information, the information may be given as voice.

Furthermore, a specific method for outputting the information such as the sound information or the light emission information recognizable by the five senses may be a conventionally known method.

In the sensor device 1 illustrated in FIG. 1, the converter 3 and the output unit 4 are connected with a wire. However, they are not necessarily connected with the wire in the sensor device of one or more embodiments of the present invention, and they may be wirelessly connected. Depending on a usage condition of the sensor device, it is sometimes more convenient that the converter and the output unit are physically separated. In this case, by giving the function of the output unit to a terminal device such as personal computer, smartphone, or tablet, the terminal device can serve as the output unit for outputting the information of such as sound, light, image, or numerical value recognizable by the five senses.

According to the above sensor device, the capacitance at the detection portion varies with the deformation (stretch) of the dielectric layer, so that when the sound information and/or the light information corresponding to the capacitance are given, the user can recognize a deformation state of the sensor element.

Therefore, for example, when the sensor element is attached to the deformable measuring object and used, its deformation state can be known.

In addition, for example, when the user actively deforms the sensor element, the sensor device can be used as an information transmitter which transmits information reflecting an intention of the user. More specifically, when the information to be transmitted is the sound information, the sensor device can be used as a sound source, voice generator or the like.

Next, a stretchable structure of one or more embodiments of the present invention will be described with reference to the drawings.

The stretchable structure of one or more embodiments of the present invention includes a stretchable apparatus body, and the sensor device integrated with the apparatus body, wherein the sensor element stretches in response to a stretch of the apparatus body.

Figure 4A:
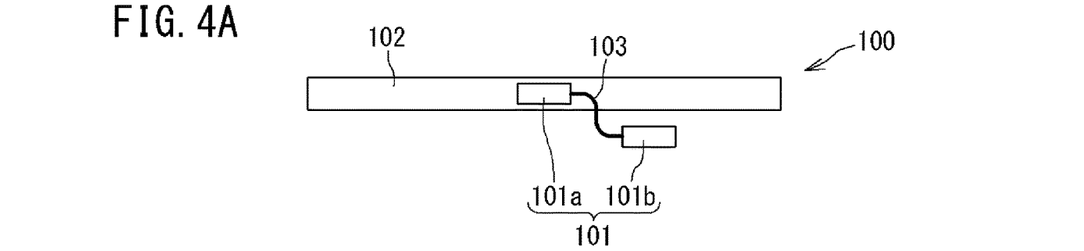
FIGS. 4A to 4E are views each illustrating one example of a stretchable structure according to one or more embodiments of the present invention.

FIG. 4A is a plan view schematically illustrating one example of the stretchable structure according to one or more embodiments of the present invention.

A stretchable structure 100 illustrated in FIG. 4A includes a band-shaped elastomer tube 102 as one example of a tube for rehabilitation (training tube) serving as the apparatus body. In the stretchable structure 100, the elastomer tube 102 and a sensor device 101 of one or more embodiments of the present invention are integrated. More specifically, a sensor element 101a of the sensor device 101 is attached to a surface of the elastomer tube 102 through an adhesive layer (not illustrated), and a display unit 101b incorporating a converter and an output unit is connected to the sensor element through a lead wire 103. Here, the adhesive layer to attach the sensor element 101a is laminated on a whole bottom surface of the sensor element 101a.

According to the stretchable structure 100, the sensor element 101a stretches in response to a stretch of the elastomer tube 102 in a longitudinal direction, and at this time, capacitance at a detection portion of the sensor element 101a varies with a stretched amount. Thus, as described above, the output unit incorporated in the display unit 101*b* outputs information such as sound or light corresponding to the detected capacitance.

Thus, the user can know a usage state of the stretchable structure, and an excise state of the user himself based on it.

When the information from the output unit in the stretchable structure of one or more embodiments of the present invention is the voice information, the user can be encouraged or praised by emitted voice depending on whether or not an elongation rate of the elastomer tube 102 has reached a predetermined elongation rate. Thus, the user can be more motivated to undergo the rehabilitation. Furthermore, when the elongation rate exceeds the predetermined elongation rate, voice may be emitted so that the user is informed of overworking.

The stretchable structure of one or more embodiments of the present invention may include a recording portion for recording a measured result in the sensor device. In this case, an excise result in the stretchable structure can be recorded. The stretchable structure including the recording portion is especially suitable for being used for the rehabilitation.

When the user takes a rehabilitation exercise under the guidance of a specialist, the specialist generally sets such as the kind, the strength, the number of times, and the frequency of the exercise in a rehabilitation apparatus for the user. Thus, in addition to being able to confirm the usage state of the stretchable structure in real time, based on the information from the output unit, when the stretchable structure used as the rehabilitation apparatus includes the recording portion, such as the kind, the strength, the number of times, and the frequency of the exercise can be recorded in the recording portion, so that a history of the daily rehabilitation training can be confirmed, and the information can be shared with the specialist, and in addition, the recorded information can be used as feedback information of the setting of the rehabilitation exercise (rehabilitation program).

The stretchable structure according to one or more embodiments of the present invention may have configurations illustrated in FIGS. 4B to 4E.

Figure 4B:
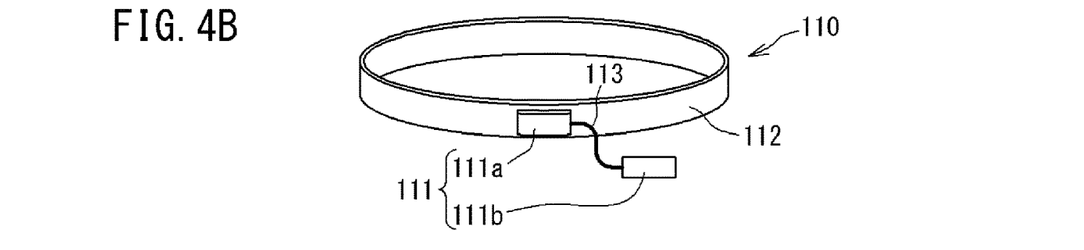

FIG. 4B is a perspective view schematically illustrating another example of the stretchable structure according to one or more embodiments of the present invention.

A stretchable structure 110 illustrated in FIG. 4B includes an endless band 112 made of elastomer and serving as one example of the tube for rehabilitation (training tube) as the apparatus body. In the stretchable structure 110, the endless band 112 and a sensor device 111 are integrated. More specifically, a sensor element 111*a* of the sensor device 111 is attached to a surface of the endless band 112 through an adhesive layer (not illustrated), and a display unit 111*b* incorporating a converter and an output unit is connected to the sensor element through a lead wire 113. Here, the adhesive layer to attach the sensor element 111*a* is laminated on a whole bottom surface of the sensor element 111*a*.

According to the stretchable structure 110, similar to the stretchable structure 100, the sensor element 111*a* stretches in response to a stretch of the endless band 112, and capacitance at a detection portion of the sensor element 111*a* varies with its stretched amount. Thus, the output unit incorporated in the display unit 111*b* outputs information such as sound or light corresponding to the detected capacitance, and the user can recognize a usage state of the stretchable structure 110 based on the information such as sound or light.

Figure 4C:
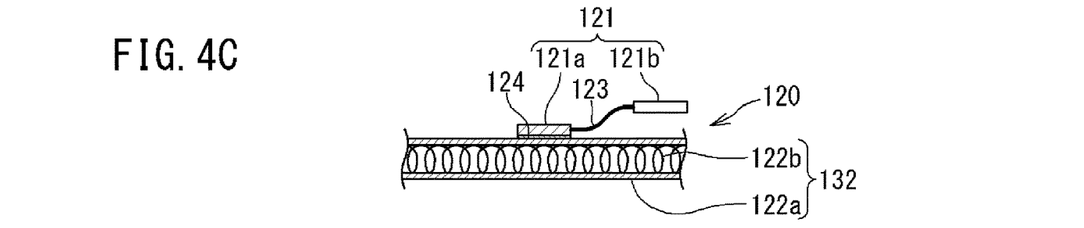

FIG. 4C is a perspective view schematically illustrating another example of the stretchable structure according to one or more embodiments of the present invention.

A stretchable structure 120 illustrated in FIG. 4C includes an expander 122 as the apparatus body wrapping a metal coil spring 122*b* in an elastomer tube 122*a*. In the stretchable structure 120, the expander 122 and a sensor device 121 of one or more embodiments of the present invention are integrated. More specifically, a sensor element 121*a* of the sensor device 121 is attached to a surface of the expander 122 with an adhesive layer 124, and a display unit 121*b* incorporating a converter and an output unit is connected to the sensor element through a lead wire 123. Here, the adhesive layer 124 is laminated on a whole bottom surface of the sensor element 121*a*.

According to the stretchable structure 120, the sensor element 121*a* stretches in response to a stretch of the expander 122, and capacitance at a detection portion of the sensor element 121*a* varies with its stretched amount. Thus, the output unit incorporated in the display unit 121*b* outputs information such as sound or light corresponding to the detected capacitance, and the user can recognize a usage state of the stretchable structure 120 based on the information such as sound or light.

Figure 4D:
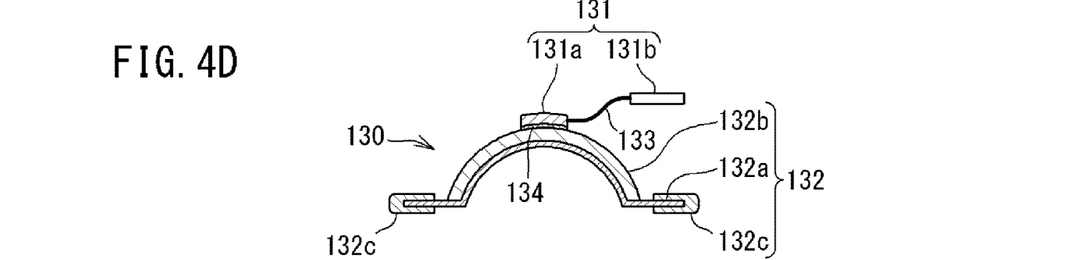

FIG. 4D is a perspective view schematically illustrating another example of the stretchable structure according to one or more embodiments of the present invention.

A stretchable structure 130 illustrated in FIG. 4D includes an apparatus body 132 including a plate spring 132*a* having a roughly arc-shaped curved portion, an elastomer layer 132*b* laminated on the curved portion, and a holder 132*c* provided at both ends of the plate spring 132*a*; and a sensor device 131 attached to the apparatus body 132. More specifically, a sensor element 131*a* of the sensor device 131 is attached to a surface of the elastomer layer 132*b* of the apparatus body 132 through an adhesive layer 134, and a display unit 131*b* incorporating a converter and an output unit is connected to the sensor element through a lead wire 133. Here, the adhesive layer 134 is laminated on a whole bottom surface of the sensor element 131*a*.

When the stretchable structure 130 is used, the user holds the holders 132*c*, and applies a load so that the curved portion is further curved in the stretchable structure 130. At this time, the elastomer layer 132*b* is stretched in accordance with a curved amount of the curved portion, and the sensor element 131*a* stretches in response to a stretch of the elastomer layer 132*b*, and capacitance at a detection portion of the sensor element 131*a* varies with its stretched amount. Thus, the output unit incorporated in the display unit 131*b* outputs information such as sound or light corresponding to the detected capacitance, and the user can recognize a usage state of the stretchable structure 130 based on the information such as sound or light.

Furthermore, in the case where the apparatus body has the configuration illustrated in FIG. 4C or 4D, that is, in the case where the apparatus body is surely deformed by use of the metal elastic member such as metal coil spring or metal plate spring, and the metal elastic member is covered with the elastomer, sufficiently soft elastomer can be used. Therefore, stress applied to the elastomer can be reduced, so that the elastomer is not likely to be fatigued, and a life of the apparatus body can be prolonged.

Figure 4E:
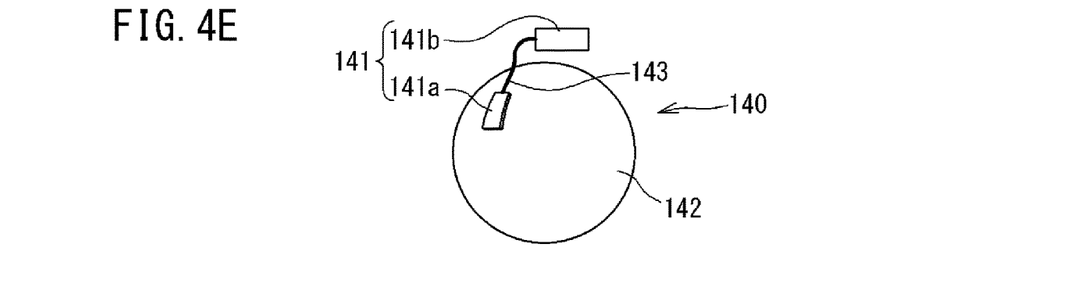

FIG. 4E is a perspective view schematically illustrating another example of the stretchable structure according to one or more embodiments of the present invention.

A stretchable structure 140 illustrated in FIG. 4E includes an elastomer ball (rubber ball) 142 as the apparatus body. In the stretchable structure 140, the rubber ball 142 and a sensor device 141 are integrated. More specifically, a sensor element 141a of the sensor device 141 is attached to a surface of the rubber ball 142 through an adhesive layer (not illustrated), and a display unit 141b incorporating a converter and an output unit is connected to the sensor element through a lead wire 143. Here, the adhesive layer is laminated on a whole bottom surface of the sensor element 141a.

In the stretchable structure 140, the sensor element 141a stretches in response to a deformation (stretch) of the rubber ball 142, and capacitance at a detection portion of the sensor element 141a varies with its stretch amount. Thus, the output unit incorporated in the display unit 141b outputs information such as sound or light corresponding to the detected capacitance, and the user can recognize a usage state of the stretchable structure 140 based on the information such as sound or light.

The apparatus body in the above stretchable structure is not limited to those illustrated in FIGS. 4A to 4E, and it only needs to be stretchable. However, if the deformation (stretch) amount of the apparatus body is too small at the time of use, the deformation amount of the sensor element which is deformed in accordance with the apparatus body is also small, and the variation amount of the capacitance of the sensor element could be too small in some cases, and in this case, the deformation amount of the apparatus body may not be accurately measured. Therefore, as for the deformation amount in the portion having the integrated (attached) sensor element in the apparatus body, an elongation deformation rate is 20% or more, and an area increase rate is about 10% or more in a normal usage state. The apparatus body having the deformation amount falling within the above-described range is especially suitable as the object in which its deformation amount is detected by the sensor device of one or more embodiments of the present invention.

The apparatus body may be the one in which the stretchability is ensured by the elastomer as illustrated in FIGS. 4A, 4B, and 4E, or may be the one composed of the metal elastic member and the elastomer member provided around the elastic member, in which the stretchability is mainly ensured by the metal elastic member as illustrated in FIGS. 4C and 4D.

Here, examples of the above elastomer include natural rubber, synthetic rubber, thermoplastic elastomer, thermosetting polyurethane, and silicone rubber.

In the case where the apparatus body is the one in which the stretchability is ensured by the elastomer, the elastomer has appropriate stretch-stress characteristics (S-S characteristics), and has small permanent elongation even after repeated stretching.

In view of being small in permanent elongation after the repeated stretching, the above elastomer is a cross-linked natural rubber, a cross-linked isoprene rubber belonging to the synthetic rubber, or thermoplastic elastomer designed to have small permanent elongation.

Furthermore, in the case where the apparatus body is directly in contact with a human body when it is used, the apparatus body is selected from the one made of material which does not contain an allergenic substance (such as protein contained in the natural rubber).

Still furthermore, the material of the elastomer may be the same as that of the dielectric layer or the protective layer in the sensor device of one or more embodiments of the present invention. In this case, the apparatus body and the sensor element are likely to show similar deformation behavior.

As illustrated in FIGS. 4A to 4E, when the sensor element is attached to the apparatus body, the adhesive layer is laminated on the whole bottom surface of the sensor element to attach the sensor element to the apparatus body. However, it is to be noted that the adhesive layer is not necessarily formed on the whole bottom surface of the sensor element, and it may be formed only in a part of the bottom surface of the sensor element. In this regard, the adhesive layer needs to be formed so that the sensor element can be deformed in accordance with the deformation of the apparatus body.

The adhesive layer may be formed of conventionally known adhesive material, and the adhesive layer should not hinder the deformations of the sensor device and the apparatus body but follow those deformations.

In addition, the method for attaching the sensor element to the apparatus body is not limited to the method using the adhesive layer, and another conventionally known adhesion (bonding) method may be used. More specifically, depending on the elastomer composition, the electroconductive composition, and the composition of the apparatus body, the sensor element and the apparatus body may be connected by a vulcanization bonding directly or through an appropriate elastomer layer.

As illustrated in FIGS. 4A to 4E, the sensor element is attached alone to the apparatus body, and the display unit integrating the converter and the output unit is separately connected to the sensor element through the lead wire. However, the stretchable structure of one or more embodiments of the present invention may be configured such that a unit integrating the sensor element and the converter may be attached to the apparatus body, and the unit may be separately connected to an output unit through the lead wire or connected thereto wirelessly. Furthermore, in the above stretchable structure, all the members of the sensor element may be attached to the apparatus body.

In the case where the output unit is connected wirelessly, the output unit can be set in a position where it does not become an obstacle to the user and can be easily recognized by the user while the stretchable structure is used.

Furthermore, according to the stretchable structure described above, the apparatus body and the sensor device are attached and integrated through the adhesive layer. However, the stretchable structure of one or more embodiments of the present invention is not limited to the case where the apparatus body and the sensor device are separately manufactured and then they are attached together, and it may include a case where both are integrated in such a manner that the apparatus body partially serves as a component member of the sensor device.

More specifically, the stretchable structure may include a case where the apparatus body and the sensor element are integrated in such a manner that a part of the elastomer apparatus body as illustrated in FIGS. 4A and 4B serves as the dielectric layer of the sensor element, and the electrode layers are formed on both surfaces of that part of the apparatus body across the apparatus body.

In the stretchable structure of one or more embodiments of the present invention, the sensor device is integrated with the stretchable apparatus body. Therefore, the user can be informed of the stretched state (usage state) according to the stretch of the apparatus body.

The stretchable structure of one or more embodiments of the present invention can be suitably used in such as a rehabilitation apparatus and a training tool.

EXAMPLES

Hereinafter, one or more embodiments of the present invention will be described more specifically with an example, but the present invention is not limited to the following example.

FIGS. 5A to 5D are perspective views to describe manufacturing steps of a sensor element in the example. FIG. 6 is a schematic view illustrating a sensor device manufactured in the example.

<Tube for Rehabilitation Having Sensor Device>

1. Apparatus Body

As the apparatus body, a commercially available tube for rehabilitation was used (Thera-Band (registered trademark), loop type # TLB-1 (imported and distributed by D&M Co., Ltd.), 90 cm (circumference)×7.5 cm (width)).

2. Manufacture of Sensor Element with Adhesive Layer (1) Manufacturing of Dielectric Layer A raw material composition was prepared for the dielectric layer by adding 40 parts by weight of plasticizer (dioctyl sulfonate) and 17.62 parts by weight of isocyanate (PANDEX GCA-11 produced by DIC Corporation) to 100 parts by mass of polyol (PANDEX GCB-41 produced by DIC Corporation), and mixing and stirring them with an agitator for 90 seconds. Then, the raw material composition was poured into the forming apparatus 30 illustrated in FIG. 3, and while it was transferred in a sandwiched state with the protective films 31, it was cross-linked and cured at a furnace temperature of 70° C. for 30 minutes in a furnace, whereby a rolled sheet with the protective films and having a predetermined thickness was manufactured. After that, the sheet was cross-linked at 70° C. for 12 hours in a furnace, whereby a sheet composed of polyether-based urethane elastomer was manufactured. After that, the manufactured urethane sheet was cut into a size of 20 mm×74 mm×100 μm (thickness), and its corner part of 10 mm×7 mm×100 μm (thickness) was cut, whereby the dielectric layer was manufactured.

In addition, break elongation (%) and relative permittivity of the manufactured dielectric layer were measured. The break elongation (%) was 505%, and the relative permittivity was 6.6.

The break elongation was measured based on JIS K 6251. The relative permittivity was found by measuring capacitance at a measurement frequency of 1 kHz with LCR HiTESTER (3522-50 manufactured by HIOKI E. E. CORPORATION) while the dielectric layer was sandwiched by electrodes of 20 mmϕ, and then making a calculation based on an electrode area and a thickness of the measurement sample.

(2) Preparation of Electrode Layer Material

Furthermore, 30 mg of multi-walled carbon nanotubes manufactured by a substrate growth method, that is, highly oriented carbon nanotubes (number of walls was 4 to 12, fiber diameter was 10 to 20 nm, fiber length was 150 to 300 μm, and carbon purity was 99.5%) produced by TAIYO NIPPON SANSO CORPORATION was added to 30 g of methyl isobuthyl ketone (MIBK), and a wet dispersion process was performed with a jet mill (Nano Jet Pul JN10-SP003 manufactured by JOKOH CO., LTD.), and diluted 10 times, whereby a carbon nanotube dispersion liquid having a concentration of 0.01% by weight was obtained.

(3) Manufacture of Protective Layer

By the same method as that used for manufacturing the dielectric layer in (1), the bottom protective layer of 20 mm×74 mm×50 μm (thickness), and the top protective layer of 20 mm×67 mm×50 μm (thickness) were manufactured of polyether-based urethane elastomer.

(4) Manufacture of Adhesive Layer

Furthermore, 2 parts by mass of curing agent (L-45 produced by Soken Chemical Engineering Co., Ltd.) was added to and mixed with 100 parts by weight of adhesive agent (SK-1720 produced by Soken Chemical & Engineering Co., Ltd.). An obtained mixture was applied to a PET film having a surface subjected to a release treatment, with a bar coater, and cured at 100° C. for 30 minutes, whereby an adhesive layer having a thickness of 50 μm after cured was manufactured.

(5) Manufacture of Sensor Element

The sensor element was manufactured through the steps illustrated in FIGS. 5A to 5D.

First, a mask (not illustrated) was prepared by forming an opening having a predetermined shape in the PET film which had been subjected to the release treatment, and attached to one side (surface) of a bottom protective layer 25B manufactured in the step (3).

The mask has the opening corresponding to the bottom electrode layer and the bottom conducting wire, and a size of the opening for the bottom electrode layer was 16 mm (width)×60 mm (length) and a size thereof for the bottom conducting wire was 5 mm (width)×10 mm (length).

After that, 7.2 g of the carbon nanotube dispersion liquid prepared in the step (2) was applied from a distance of 10 cm with an air brush, and dried at 100° C. for 10 minutes, whereby a bottom electrode layer 22B and a bottom conducting wire 23B were formed. After that, the mask was removed (refer to FIG. 5A).

After that, a dielectric layer 21 manufactured in the step (1) was attached and laminated on the bottom protective layer 25B so as to cover the whole of the bottom electrode layer 22B and a part of the bottom conducting wire 23B.

Figure 5A:
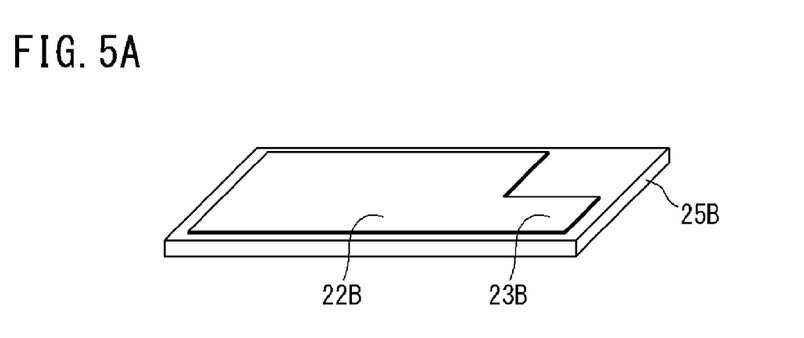
FIGS. 5A to 5D are perspective views to describe manufacturing steps of a sensor element in an example.
Figure 5B:
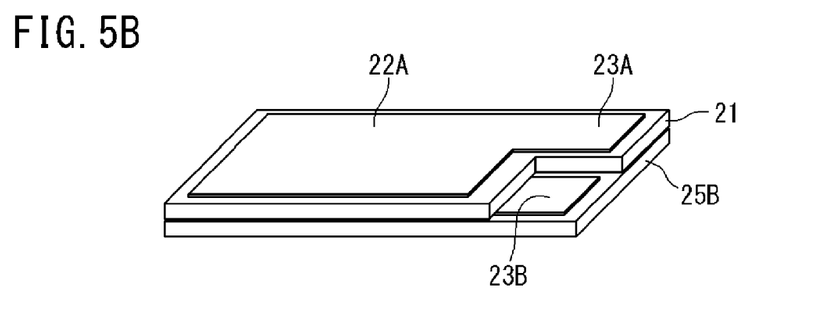
Figure 6:
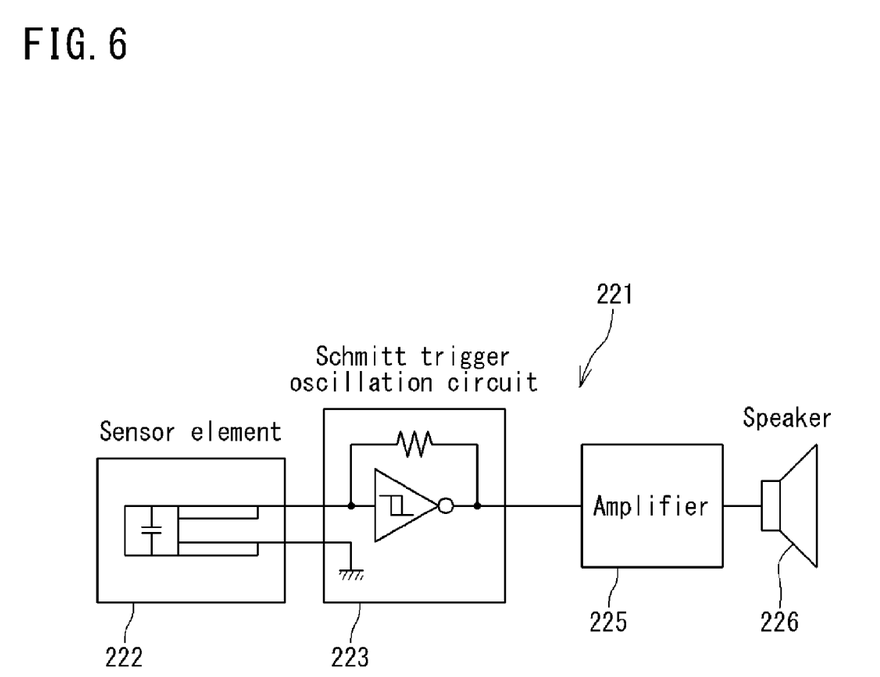
FIG. 6 is a schematic view illustrating a sensor device manufactured in the example.

Furthermore, a top electrode layer 22A and a top conducting wire 23A were formed on a top side of the dielectric layer 21 by the same method as that used for forming the bottom electrode layer 22B and the bottom conducting wire 23B (refer to FIG. 5B).

After that, a top protective layer 25A manufactured in the step (3) was laminated with a laminator on the top side of the dielectric layer 21 having the top electrode layer 22A and the top conducting wire 23A so as to cover the whole of the top electrode layer 22A and a part of the top conducting wire 23A.

Figure 5C:
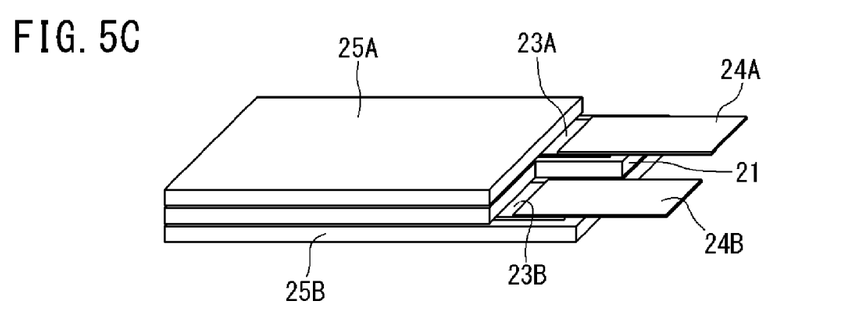

Furthermore, a top connecting portion 24A and a bottom connecting portion 24B were formed by attaching copper foil to ends of the top conducting wire 23A and the bottom conducting wire 23B, respectively (refer to FIG. 5C). After that, a lead wire 29 serving as an external conducting wire was fixed with solder to each of the top connecting portion 24A and the bottom connecting portion 24B.

Subsequently, a PET film 27 for reinforcement having a thickness of 100 μm was attached to portions of the top connecting portion 24A and the bottom connecting portion 24B positioned on the bottom protective layer 25B through an acrylic adhesive tape (having a thickness of 0.5 mm) (Y-4905 produced by 3M Company) 26.

Figure 5D:
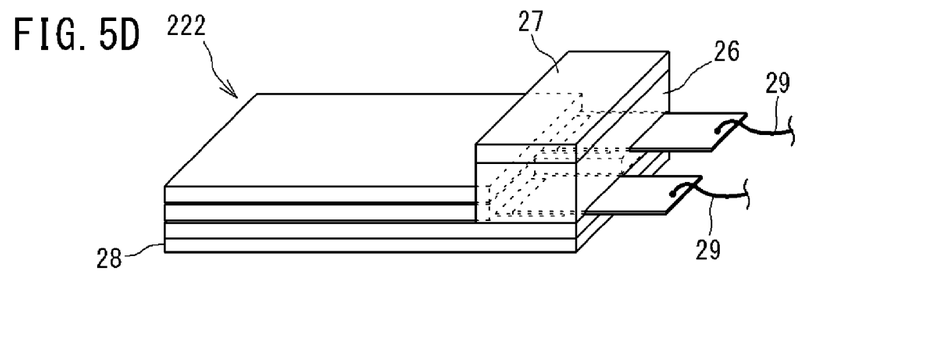

Finally, an adhesive layer 28 manufactured in the step (4) was laminated to the bottom surface of the bottom protective layer 25B, whereby a sensor element 222 was completed (refer to FIG. 5D).

3. Manufacture of Stretchable Structure (Tube for Rehabilitation)

The sensor element with the adhesive layer manufactured in the process 2 was attached and fixed to the surface of the apparatus body.

After that, the converter and the output unit were connected to the sensor element, whereby the stretchable structure was manufactured.

The configuration of the sensor device in the stretchable structure is illustrated in FIG. 6.

As illustrated in FIG. 6, in a sensor device 221, the sensor element 222 manufactured through the steps (1) to (5) was connected to a Schmitt trigger oscillation circuit (oscillation frequency at non-elongation: 1 KHz) 223, and connected to a speaker 226 (K36WP manufactured by VISATON GmbH & Co. KG) through an audio amplifier 225 (LM4889 manufactured by Texas Instruments Incorporated).

In addition, in the Schmitt trigger oscillation circuit 223, a Schmitt Inverter (model number: TC7W14F) manufactured by Toshiba Semiconductor & Storage Products Company) was used as the Schmitt trigger inverter IC, and a resistor is composed of a fixed resistor and a variable resistor, in which a total resistance value was about 1.8 MΩ, and the oscillation frequency at non-elongation was set at 1 kHz through fine adjustment with the variable resistor.

4. Operation Verification of Stretchable Structure (Tube for Rehabilitation)

It was confirmed that when the stretchable structure (the dielectric layer of the sensor element 222) manufactured in the process 3. was elongated by 100% (elongated 2 times), the capacitance at the detection portion was increased about 2 times, and an oscillation frequency from the Schmitt trigger oscillation circuit was decreased about ½ time. Furthermore, it was confirmed that when the stretchable structure (the dielectric layer of the sensor element 222) was elongated by 200% (elongated 3 times), the capacitance of the detection portion was increased about 3 times, and the oscillation frequency from the Schmitt trigger oscillation circuit was decreased about ⅓ time.

In addition, it was also confirmed that as the stretchable structure is elongated, sound from the speaker 26 is changed from high pitch sound to low pitch sound.

REFERENCE SIGNS LIST 1, 101, 111, 121, 131, 141, 221: SENSOR DEVICE
2, 101a, 111a, 121a, 131a, 141a, 222: SENSOR ELEMENT
3: CONVERTER
3a, 223: SCHMITT TRIGGER OSCILLATION CIRCUIT
3b: F/V CONVERSION CIRCUIT
4: OUTPUT UNIT
4a: PIC CONTROL CIRCUIT
4b: LED DISPLAY
11, 21: DIELECTRIC LAYER
12A, 22A: TOP ELECTRODE LAYER
12B, 22B: BOTTOM ELECTRODE LAYER
13A, 23A: TOP CONDUCTING WIRE
13B, 23B: BOTTOM CONDUCTING WIRE
14A, 24A: TOP CONNECTING PORTION
14B, 24B: BOTTOM CONNECTING PORTION
15A, 25A: TOP PROTECTIVE LAYER
15B, 25B: BOTTOM PROTECTIVE LAYER
28: ADHESIVE LAYER
100, 110, 120, 130, 140: STRETCHABLE STRUCTURE
101b, 111b, 121b, 131b, 141b: DISPLAY UNIT
102: ELASTOMER TUBE
112: ENDLESS BAND
122: EXPANDER
132: APPARATUS BODY
142: RUBBER BALL
225: AUDIO AMPLIFIER
226: SPEAKER

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A sensor device comprising:
   a sensor element comprising:
      a sheet-like dielectric layer comprising an elastomer composition; and
      a top electrode layer and a bottom electrode layer each comprising an electroconductive composition containing carbon nanotubes, wherein:
      the top and the bottom electrode layers are formed on a top surface and a bottom surface of the dielectric layer, respectively, and are at least partially opposed to each other across the dielectric layer,
      the at least partially opposed portions of the top and the bottom electrode layers constitute a detection portion, and
      the dielectric layer is reversibly deformed in a surface plane direction to change an area of a main surface of the dielectric layer;
   a converter electrically connected to the sensor element that converts capacitance at the detection portion that varies in accordance with the deformation of the dielectric layer to electric characteristics; and
   an output unit that outputs information corresponding to the electric characteristics, wherein the information is at least sound information.

2. The sensor device according to claim 1, wherein the dielectric layer is deformable to an extent that the area of the main surface is increased from a non-elongation state by 30% or more.

3. The sensor device according to claim 1, wherein the information is at least sound information and light information.

4. The sensor device according to claim 1, wherein the output unit changes the sound information depending on a change of the capacitance.

5. A stretchable structure comprising:
   a stretchable apparatus body, and the sensor device according to claim 1, the sensor device being integrated with the apparatus body, wherein
   the sensor element stretches in response to a stretch of the apparatus body.

6. The stretchable structure according to claim 5, wherein the apparatus body is an expander or a tube for rehabilitation.

* * * * *